United States Patent
Geary et al.

Patent Number: 5,269,803
Date of Patent: Dec. 14, 1993

[54] HEMOSTASIS PRESSURE PAD BAND

[75] Inventors: Gregory L. Geary, Portland; Thomas R. Tribou, West Linn, both of Oreg.; Delbert L. Rice, Vancouver, Wash.

[73] Assignee: GTR Patent, Inc., Vancouver, Wash.

[21] Appl. No.: 867,170

[22] Filed: Apr. 10, 1992

[51] Int. Cl.$^5$ .......................................... A61B 17/00
[52] U.S. Cl. .................................................. 606/201
[58] Field of Search ............. 606/201, 202, 203, 204; 602/53, 58, 42; 128/887, 888

[56] References Cited

U.S. PATENT DOCUMENTS

| | | |
|---|---|---|
| 1,426,124 | 8/1922 | Thomas . |
| 1,561,116 | 11/1925 | Silliman . |
| 1,607,208 | 11/1926 | Pease . |
| 2,367,690 | 1/1945 | Purdy . |
| 2,712,314 | 7/1955 | Kohl . |
| 3,265,064 | 8/1966 | Gruber . |
| 3,779,249 | 12/1973 | Semler . |
| 4,182,338 | 1/1980 | Stanulis . |
| 4,314,568 | 2/1982 | Loving . |
| 4,572,182 | 2/1986 | Royse . |
| 4,742,825 | 5/1988 | Freund et al. . |
| 4,829,994 | 5/1989 | Kurth . |
| 5,010,902 | 4/1991 | Rambo et al. . |

*Primary Examiner*—Stephen C. Pellegrino
*Assistant Examiner*—William Lewis
*Attorney, Agent, or Firm*—Keith A. Cushing

[57] ABSTRACT

A hemostasis pressure pad band is shown and described including a controllably adjustable band for tightening about a patient's limb and a needle site contacting pad which bears against a needle site at the time of needle removal to prevent bleeding therefrom. The pad includes a pair of cheek formations which define a channel along and in which a graft is positioned prior to needle removal. The channel formation may further include a ridge formation of its base and along its length which further defines side channels for better permitting circulation while engaging the needle site. The pad also includes a notch formation at one end of the channel for accommodating the inclined needle at the needle site prior to its removal.

20 Claims, 4 Drawing Sheets

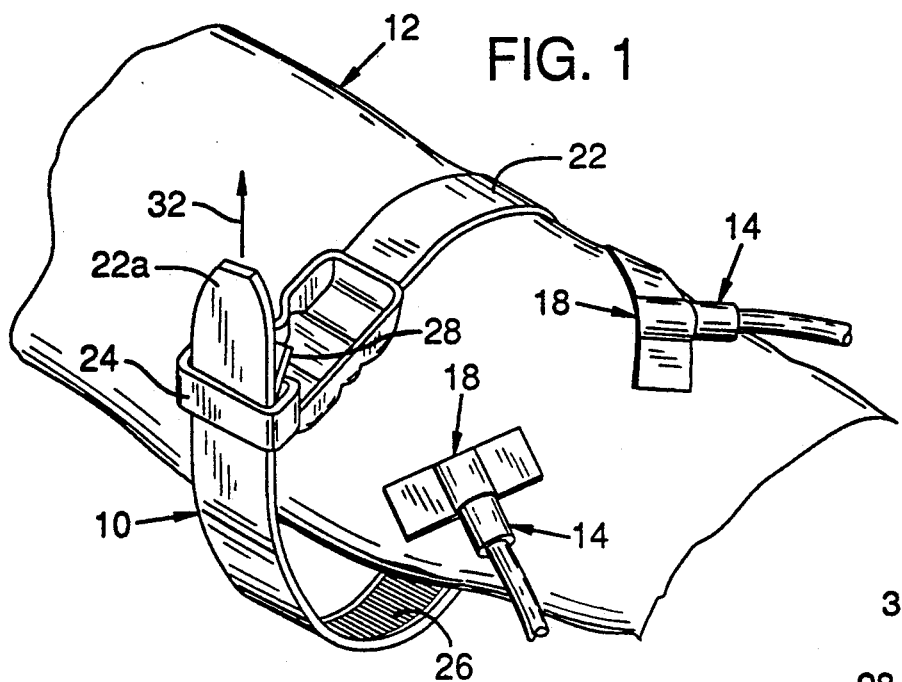
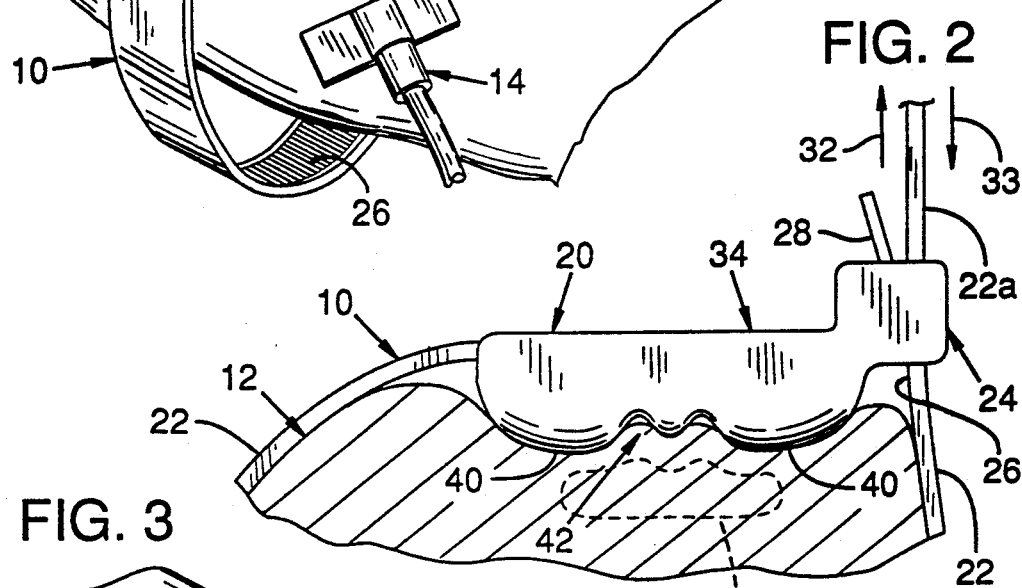
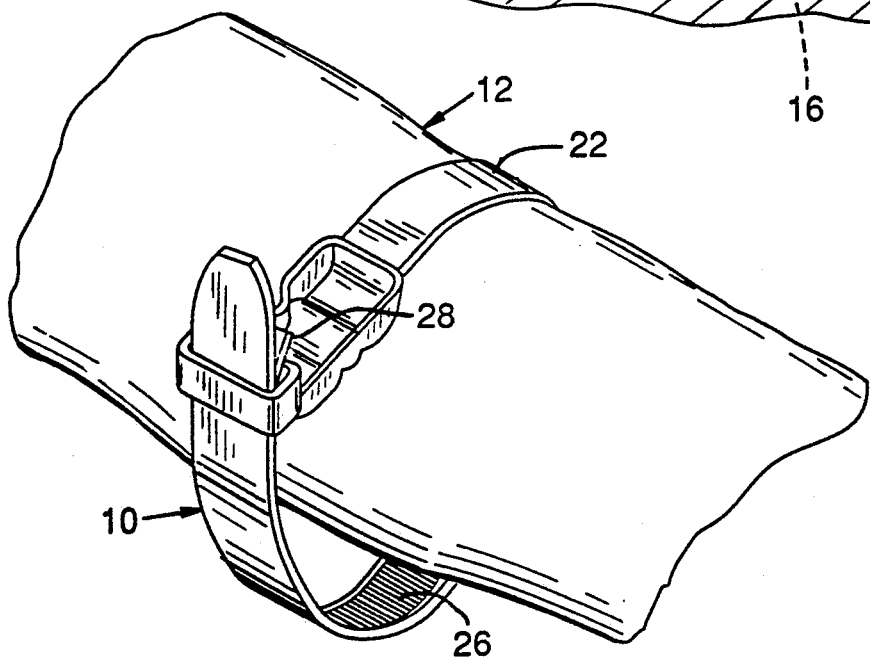

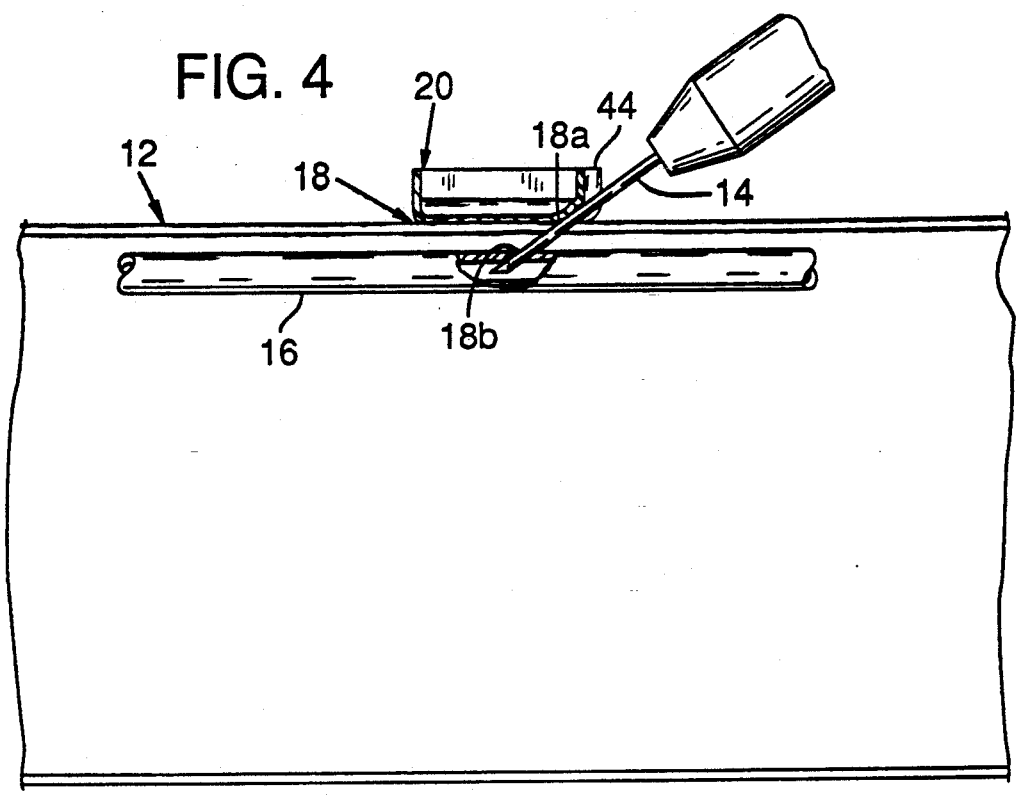
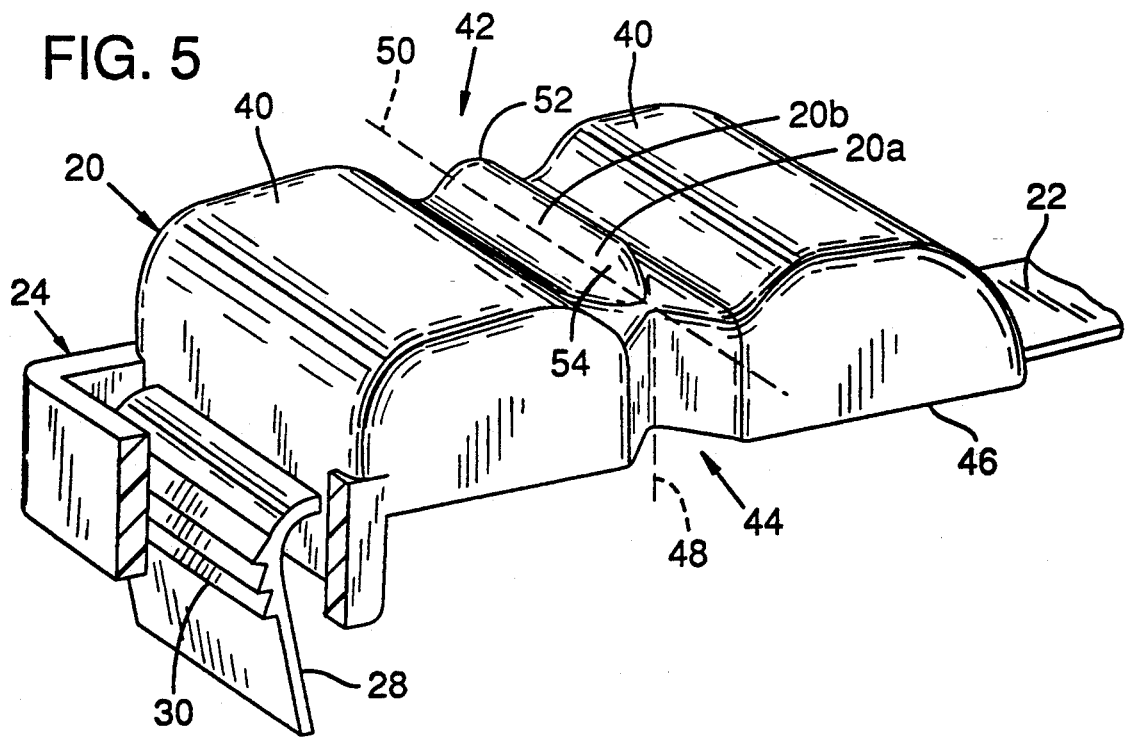

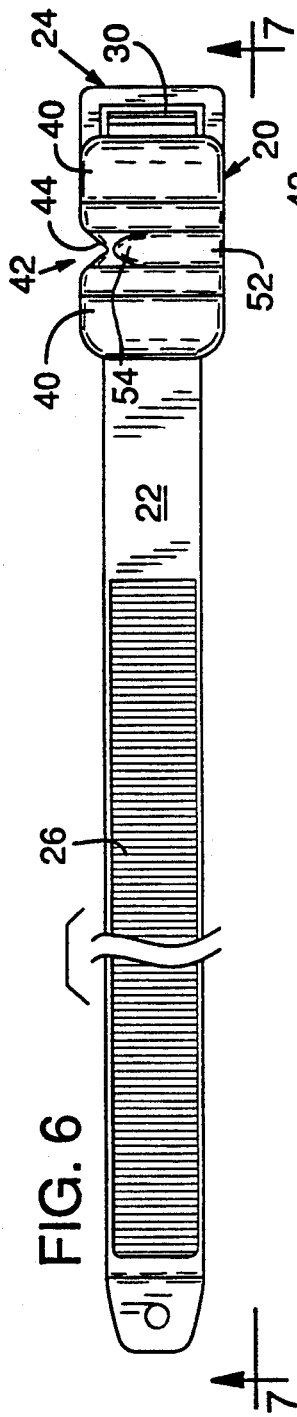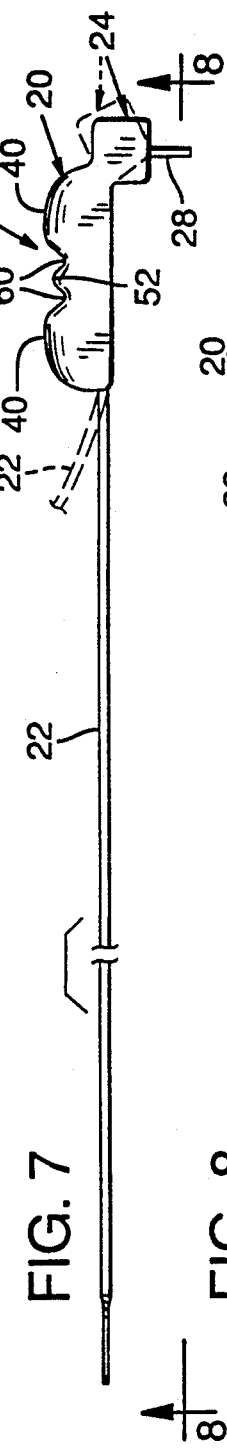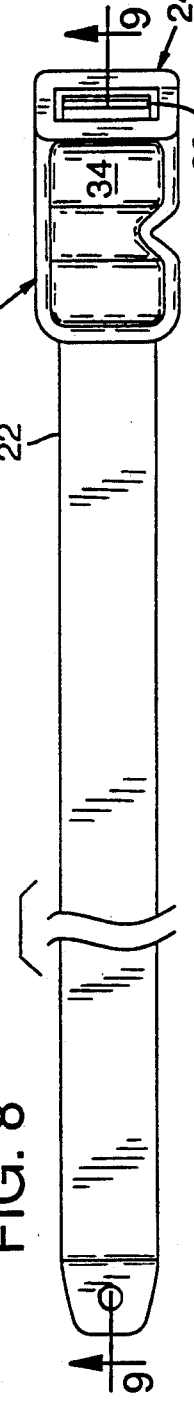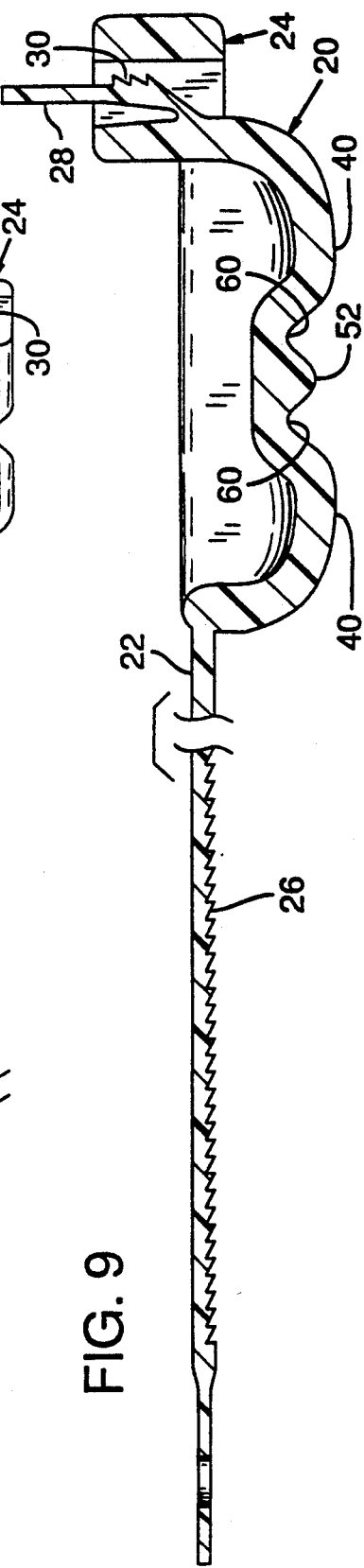

_HEMOSTASIS PRESSURE PAD BAND_

BACKGROUND OF THE INVENTION

The present invention relates generally to medical devices for applying pressure to a puncture site to aid hemostasis of the puncture site, i.e., blood clotting, for sealing the puncture site, and particularly to a hemostasis pressure pad carried upon an adjustable band or strap for convenient and single use.

Certain medical procedures require insertion of a needle into an artery or a vein of the patient, either momentarily or under prolonged circumstances, to inject or withdraw fluids into and from the blood circulatory system. Withdrawal of the needle from the artery or vein requires immediate application digital pressure to the puncture site to prevent blood flow, and requires continued application of pressure for sufficient time to allow natural blood clotting to seal the puncture site. The applied digital pressure must be present for a significant time, e.g., on the order of 15 minutes, for the blood to clot and seal the puncture wound by way of the body's own nature healing process.

For example, persons suffering kidney impairment cannot maintain a clean blood supply and must have their blood supply cleansed by a dialysis or artificial kidney machine. In such procedures, the kidney machine is temporarily integrated into the blood circulatory system to remove blood from a vein, i.e., blood carrying impurities from body organs and tissues; filter that blood within the artificial kidney machine; and return the cleansed blood to the circulation system at an artery for delivery to the body organs and tissues in the normal course. Thus, to perform dialysis the patient's blood system is accessed at two locations, i.e., to take and return blood. Such access is accomplished by inserting needles through the skin and into the blood circulatory system.

For most dialysis patients, however, the repeated access to the blood system by needles would damage the veins and arteries. To avoid such damage, grafts are placed under the skin surface and in series with the blood system to allow frequent access by needle to the blood system without repeatedly puncturing the patient's veins and arteries.

When the dialysis treatment is complete, the needles are removed, but the associated bleeding must be controlled until the patient's natural healing process, i.e., blood clotting, seals the access site to the blood system. Thus, as each needle is withdrawn from the body, either the medical attendant or the patient must maintain digital pressure against the puncture site until hemostasis, i.e., sufficient natural blood clotting to seal the puncture, is achieved. Typically such digitally applied pressure has required up to 15 minutes before achieving hemostasis.

The process of aiding hemostasis by application of pressure has been performed by trained medical personnel with their fingers applying the needed pressure. Devices have been developed to simulate the required manual digital pressure in aid of hemostasis to more quickly free the medical attendant for other duties.

For example, U.S. Pat. No. 4,829,994 issued May 16, 1989 to Kurth shows a pelvic apron including a groin strap for securing what is described as a shaped mass or "pellet" in position over an incision in the femoral artery following catheterization of the patient. The pellet provides direct pressure upon the incision site by virtue of the contour of the pelvic apron piece and groin strap which, when wrapped about the body, secures and presses the "pellet" over the incision point to thereby halt the flow of blood until the artery repairs itself by natural clotting of the blood.

The objective of the Kurth device is to provide a sector of a sphere with a flatten pole to serve as a replacement for the equivalent amount of folded gauze to define the pressure point against the femoral arterial or venous incision, but this objective reveals the inadequacy of such a pellet formation for the intended purpose. In particular, the skin contacting surface of the pellet contacts the incision point at the artery as well as a significant area of skin immediately adjacent the artery. The large surface area of the pellet in contact with the skin distributes the downward force created by the pelvic apron and groin strap over an equal amount of skin surface. Since the diameter of the pellet is stated to be approximately 2 and ⅛ inches, the skin area onto which the downward force is distributed can be taken as being approximately a circle having a diameter of 2 and ⅛ inches with the incision site at the artery being at the center of the circle. This distribution of force over the surrounding area of the incision site requires that a significant amount of pressure be applied to the pellet by the pelvic apron and groin strap such that the pellet may stop the bleeding from the artery. Even with such strong pressure applied to the pellet, the artery can require a significant period of time to heal due.

U.S. Pat. No. 4,182,338 issued Jan. 8, 1980 to Stanulus shows a pressure appliance having a truncated, pyramid-shaped body and a cylindrical pressure applicator. Although the pressure appliance of the Stanulus device attempts to provide a localized pressure point for the applicator as disposed upon a generally flat surface of the appliance, it fails to effectively direct pressure to the artery itself. Instead, the downward force of the applicator and the surrounding surface as applied by securing straps is distributed in the area of the skin surrounding the artery or vein. The skin-contacting surfaces of the applicator and its surrounding surface lie in spaced, parallel planes whereby any pressure directed toward the skin of the body is distributed over an area of skin equaling the dimensions of the rectangular surface surrounding the applicator. The blunt end of the applicator further indents the skin an equal distance along all points defined by the surface of the applicator at its blunt end. The artery in this situation is then receiving the same amount of pressure as in the surrounding area of skin contacted by the blunt end of the applicator and, to a slightly lesser extent, the surrounding area of skin contacted by the surface about the applicator is receiving the same amount of pressure.

U.S. Pat. No. 5,010,902 issued Apr. 30, 1991 to Rambo discloses a compression orb for use in combination with appropriate bandages to apply a direct force to an arterial or venous puncture site. The device directs and focuses pressure upon the arterial or venous puncture site such that bleeding therefrom is blocked while normal systemic arterial pressure is maintained. Also, at the same time the device allows visual inspection of the puncture site.

U.S. Pat. No. 4,572,182 issued Feb. 25, 1986 to Royse and entitled Notched Pressure Pad For An Artery Clamp shows a clamp stand with an arm extending therefrom and carrying at its distal end a notched pressure pad as an artery clamp. The skin contacting surface of the pad is presented as a generally flat disk shaped member having a V-shaped notch cut therein. Other than the V-shaped notch, the undersurface, i.e., skin contacting surface, of the pad is generally flat. The notch accommodates the inclined orientation of the needle for placement of the pad prior to needle removal.

U.S. Pat. No. 4,742,825 issued May 10, 1988 to Freund et al and entitled Adjustable Compress Apparatus also shows a clamp arrangement including an arm carrying at its distal end a compress pad. The undersurface of the pad, i.e., the skin contacting portion, is generally planar, but includes a relief area in the undersurface which is spaced at its closed inner end from the center of the pad and is extended therefrom to an open outer end at a peripheral edge portion of the pad. The presence of the relief area allows catheter removal with the pad in place and provides a means of locating the pad properly with respect to the puncture site. Due to the shallowness of the groove, the pad applies pressure to the patient's skin in the region of the groove.

U.S. Pat. No. 3,779,249 issued Dec. 18, 1973 to Semler and entitled Artery Clamp shows an artery clamp having an arm carrying at its distal end a pad. The undersurface of the pad, i.e., the skin contacting surface, appears to be a planar surface bearing upon the puncture site to be compressed. More particularly, the pressure pad is described as a "generally disk shaped base on top of which is formed an integral mounting boss."

Other instruments used in connection with accessing a patient's blood circulatory system relate to the stabilization of the blood vessel during access, but do not contemplate use in aid of hemostasis.

U.S. Pat. No. 2,712,314 issued Jul. 5, 1955 to G. C. Kohl and entitled Anesthesia Needle Guide shows a handheld device for permitting injections of anesthetics locally into the wall of a cavity within the human body. The device appears to be directed towards the positioning of a guide relative to a desired puncture site and the use of the guide to bring the needle to the selected puncture site.

U.S. Pat. No. 4,314,568 issued Feb. 9, 1982 to Loving and entitled Vascular Stabilizer shows a disposable device for stabilizing a vessel during access thereto by a needle. The device includes two half body portions, each half body portion having a vascular stabilizing rib thereon such that the stabilizing ribs may be brought along the sides of a blood vessel. The vessel is then held in place for access thereto by a needle. The device has no mechanism for applying pressure to the puncture site of the needle following needle removal.

U.S. Pat. No. 1,561,116 issued Nov. 10, 1925 to Silliman shows a vein stabilizer comprising generally a planar surface held against a patient's skin and including a notch in the planar structure. The vein may be positioned along the notch in order to stabilize the vein during access by a needle. The device has no structure for applying pressure to the puncture site of the needle.

While the above described hemostasis appliances have been successful in achieving hemostasis, the pressures applied and time required to achieve hemostasis as well as an ability to maintain the appliances sanitary have not been completely satisfactory. Also, most existing hemostasis appliances are difficult to attach to the patient, and typically require two hands for placement, alignment, and engagement of the pad against the puncture site. Accordingly, it is desirable that a hemostasis appliance more conveniently apply the required pressure to a puncture site and more efficiently, i.e, quickly, achieve hemostasis

SUMMARY OF THE INVENTION

The present invention provides a hemostasis appliance for use after removal of needles following, for example dialysis, in order to apply pressure to a puncture site, yet does not occlude the vein, artery, or graft. The present invention contemplates further an arterial or venous hemostasis apparatus with either a fixed pad or a movable pad on a band which may be selectively tightened and locked about a patient's appendage. Furthermore, the adjustable strap under the present invention can be tightened or released by a locking latch or releasing latch by one-handed operation.

In accordance with the above objective, the present invention includes a hemostasis apparatus for application to an arterial or venous puncture site to simulate manual digital pressure hemostasis. The hemostasis appliance of the present invention includes an adjustable strap with either a built-in or movable hemostasis pad. The skin contacting surface of the pad includes a pair of cheek structures defining therebetween a channel. In a preferred embodiment, a ridge lying along the base of the channel defines a generally convex-concave channel formation between the cheeks. The convex-concave channel is placed over vessel just prior to removing a needle therefrom. The pad is tightened down to suitably apply pressure to the puncture site as the needle is removed. Due to the configuration of the skin contacting surface of the pad, the pad does not occlude the vessel and thereby allows continued circulation of blood therethrough. Furthermore, in the preferred embodiment, the hemostasis appliance is constructed of a substantially clear plastic material such that the puncture site is visible when the appliance is applied to a puncture site. The device may be employed as a pre-sanitized and disposable single-use product.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which:

FIG. 1 shows placement of the hemostasis pad on a patient's arm for the purpose of aiding hemostasis following removal of a needle.

FIG. 2 illustrates in section the patient's arm and the relative positioning between the hemostasis pad and a graft under the patient's skin.

FIG. 3 illustrates removal of the hemostasis pad of the present invention following hemostasis.

FIG. 4 is a side sectional view of the patient's arm, the hemostasis pad, and a needle following placement of the hemostasis pad of the present invention and prior to removal of the needle.

FIG. 5 illustrates in perspective the skin contacting surface features of the hemostasis pad of the present invention.

FIG. 6 is a top view of the hemostasis pad and associated band of the present invention.

FIG. 7 is a side view of the hemostasis pad of FIG. 6 as taken along lines 7—7 of FIG. 6.

FIG. 8 is a bottom view of the hemostasis pad as taken along lines 8—8 of FIG. 7.

FIG. 9 is a sectional view of the hemostasis pad as taken along lines 9—9 of FIG. 8.

DETAILED DESCRIPTION OF THE PREFERRED EMBODIMENTS

Figure 10:
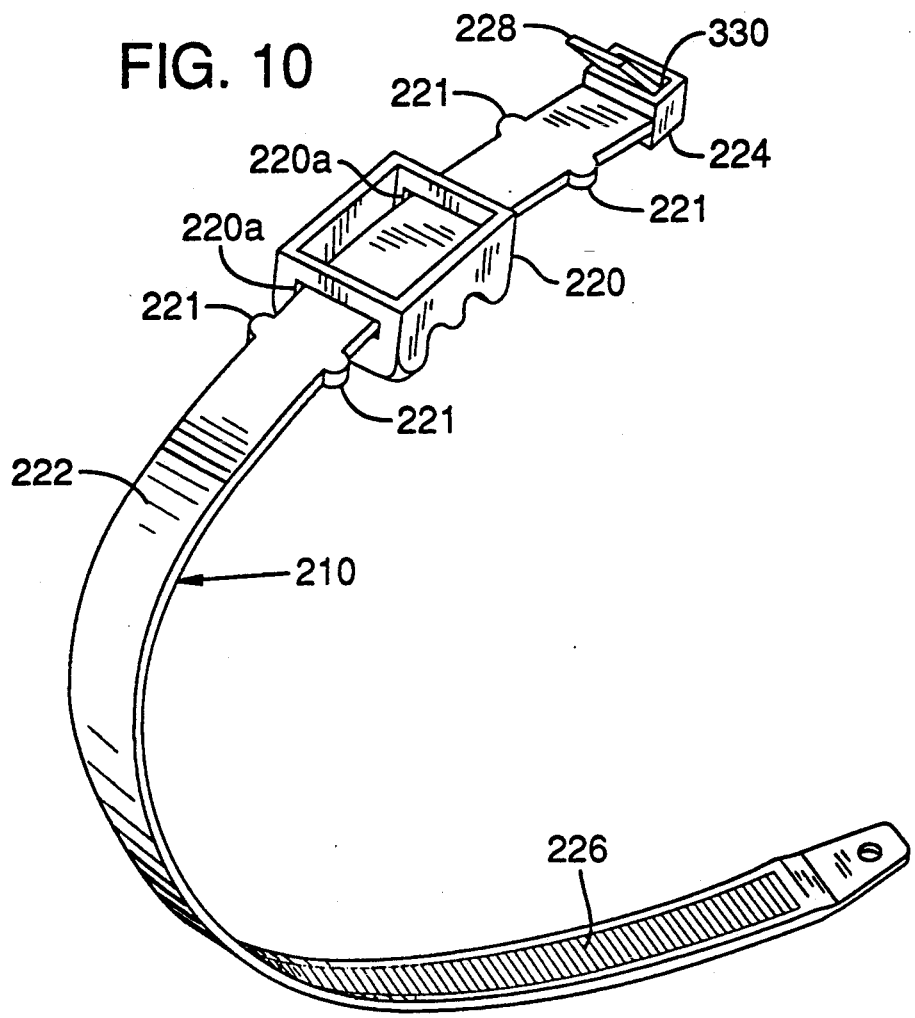
FIG. 10 illustrates in perspective an alternative embodiment of the present invention showing a hemostasis pad slidably mounted upon a band.

FIGS. 1-4 illustrate use of a hemostasis pressure pad band 10 on a patient's arm 12 according to the present invention. The function of band 10 is to aid in the removal of a needle 14 from a vein, artery or vessel 16 of arm 12. As used herein, the term "vessel" shall refer to any such portion of a fluid, e.g., blood circulatory system carrying body fluid. The band 10 is positioned over the needle site 18 prior to needle removal and bears against the needle site 18 while the needle 14 is removed. Band 10 remains bearing against the needle site 18 to simulate the digital pressure otherwise required to prevent bleeding from the needle site 18. Once hemostasis, i.e., sufficient blood clotting to seal the puncture site, is achieved the band 10 is removed (FIG. 3). The band 10 is made of plastic material, e.g., flexible polymer material, and may be pre-sanitized and pre-packaged for sanitary and convenient use as a single-use disposable product.

The hemostasis pressure pad 10 includes a skin contacting pad 20 carrying on one side a strap 22 and, on the other side, a locking arrangement 24. The locking arrangement 24 receives the distal end 22a of strap 22 and allows strap 22 to encircle the arm 12 and be controllably tightened against arm 12 with the pad 20 over the needle site 18. The strap 22 includes a serrated inner surface 26 and the locking arrangement 24 includes a release tab 28. The release tab 28 carries a similar, but oppositely directed, serrated surface 30 for engaging the serrated inner surface 26 of strap 22 to allow self-locking tightening movement 32 of distal end 22a through locking arrangement 24, but prevents loosening movement 33 or retraction from locking arrangement 24. To allow such loosening movement 33 of the distal end 22a within locking arrangement 24, the release tab 28 is moved away from strap 22 and strap 22 moves freely.

The configuration of pad 20, strap 22, and locking arrangement 24 allows convenient and one-handed installation of band 10 upon arm 12 by the medical attendant. More particularly, once the distal end 22a of strap 22 has been inserted through locking arrangement 24 sufficient distance to enable finger grasping of the distal end 22a, the attendant extends the thumb toward and engages the backside 34 of pad 20 (FIG. 2) to accomplish tightening of band 10 about arm 12 by further extending the thumb relative to the fingers and moving the distal end 22a in tightening movement 32 relative to the backside 34 of pad 20. As may be appreciated by those practicing the task of needle removal, the one-handed operation of band 10 makes more convenient the removal of the needle 14 with the other, i.e., free, hand. Should the band 10 be inadvertently overtightened upon the arm 12, the band may also be loosened with one-hand. In particular, the attendant again grasps with fingers the distal end 22a of strap 22 in the vicinity of locking arrangement 24 and extends the thumb to engage the release tab 28 to allow loosening movement 33 of the distal end 22a in the loosening direction 34 relative to locking arrangement 24.

Turning now specifically to FIG. 2, the skin contacting surface of pad 20 defines a pair of cheeks 40 having therebetween a channel 42 lying transverse to the longitudinal axis of band 22 and parallel to vessel 16. In placing the pad 20 over the needle site 18 the vessel 16 is thereby positioned along the channel 42 and the cheeks 40 rest along opposite sides of the vessel 16. In placing the pad 20 against the vessel 16 and bringing the pad 20 to bear against the needle site 18, the pad 20 should apply only sufficient pressure to hold back a flow of blood from needle site 18 upon the removal of needle 14, but should not apply such magnitude of pressure against the needle site 18 to occlude the vessel 16. Once the vessel 16 is suitably positioned within the channel 42 with cheeks 40 on either side and the strap 22 is suitably adjusted for the appropriate magnitude of pressure of pad 20 against needle site 18, the needle 14 is removed. The band 10 is left in place, as shown in FIG. 2, for sufficient time to allow hemostasis. FIG. 3 illustrates the removal of band 10 from arm 12 following hemostasis. More particularly, the tab 28 is released and band 22 is removed from locking arrangement 24.

With conventional methods of applying or simulating the application of digital pressure at a needle site, hemostasis can require 10 to 15 minutes. With use of the hemostasis pressure pad band 10 of the present invention, however, hemostasis can be achieved in as short as 2 to 3 minutes. This not only relieves the attendant or patient of the necessity of applying digital pressure for a prolonged time, the patient more quickly achieves an acceptable condition for release from direct attention, i.e., more quickly achieves hemostasis.

FIG. 4 illustrates the position of pad 20 relative to the needle site 18 just prior to removal of needle 14. Because the needle 14 is inclined relative to the vessel 16, the needle site includes two separate incisions of interest. The needle site 18 includes an incision 18a in the skin of arm 12 and an incision 18b in the vessel 16. The pad 20 includes a notch 44 for accommodating the angular orientation of needle 14 relative to the arm 12 such that needle 14 rests at the lower end of the apex of notch 44 and the reference point 20a of pad 20 (FIG. 5) lies above the incision 18a and the reference point 20b of pad 20 (FIG. 5) lies above the incision 18b. In such position, the needle 14 may then be retracted from the arm 12 by way of notch 44 while the pad 20 remains in place to halt the flow of blood from incision points 18a and 18b.

FIG. 5 shows in greater detail the skin contacting surface contour of the pad 20. In FIG. 5, the cheeks 40 are shown each including a generally flat portion lying along the channel 42. Channel 42 is open at both ends. The notch 44 is taken at the leading edge 46 of pad 20. Notch 44 defines as its apex a line 48 generally orthogonal to the channel 42. The base of channel 42, as defined by the line 50 in FIG. 5, carries a ridge 52 lying along the base of channel 42 and extending toward the notch 44. More particularly, the ridge 52 terminates in a semiconic formation 54 near the apex 48 of notch 44. With the ridge 52 so lying along the channel 42, the skin contacting surface of pad 20 may be generally characterized as a convex-concave contour whereby the channel 42 defines a concave formation and the ridge 52 lying at the base of channel 42 provides the convex feature of this contour. Experiments have shown that the band 10 works well, i.e., achieves hemostasis, without a ridge 52. However, these experiments have shown that the ridge 52 enhances operation of band 10 by achieving more quickly a condition of hemostasis.

With reference to FIGS. 4 and 5, the semi-conic formation 54 at the leading end of ridge 52 lies along the needle 14 just prior to needle 14 removal. The reference point 20a of pad 20, i.e., that which overlies the incision 18a, is found at the beginning or base of the semi-conic formation of ridge 52 and the reference point 20b of pad 20 lies along ridge 52 some distance spaced from the point 20a in a direction opposite from the notch 44. The needle 14 thereby lies generally along the semi-conic formation 54 and angularly through the notch 44 as it passes by the pad 20. In this position, the pad 20 is desirably aligned relative to the vessel 16 by placement of the reference points 20a and 20b over the incisions 18a and 18b, respectively.

FIG. 6-9 illustrate in greater detail the structure of the band 10. In FIGS. 6-9, the ridge 52 is seen as lying along the channel 42. The serrated inner surface 26 of strap 22 lies on the same side of strap 22 as does the skin contacting surface of pad 20. FIG. 9 details the release tab 28 and its serrated surface 30 which, in cooperation with the serrated surface 26 of strap 22, allows selected self-locking tightening of the band 10 about the arm 12.

The ridge 52 along the base of channel 42 defines a pair of side channels 60 lying along either side of ridge 52. Side channels 60 are believed to allow better circulation within the vessel 16 during use of band 10. More particularly, when the pad 20 comes to bear against the needle site 18, it is important that circulation within vessel 16 be maintained. The side channels 60 provide an open ended relief contour along the vessel 16 which has less occluding effect on the vessel 16 for a given magnitude of pressure against the needle site 18. Thus, the side channels 60 are believed to allow a greater range of acceptable pressure magnitudes of pad 20 against needle site 18 while maintaining circulation in the vessel 16.

Figure 11:
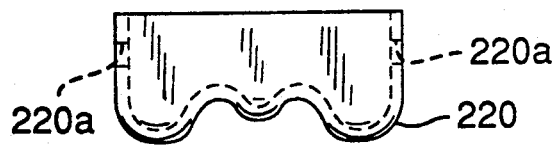
FIGS. 11 and 12 show end and side views of the hemostasis pad of FIG. 10 illustrating a slot formation for slidable mounting upon the band.
Figure 12:
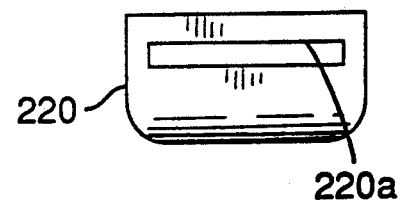

FIG. 10 illustrates a hemostasis pressure pad band 210 according to a second embodiment of the present invention. In FIG. 10, the band 210 includes a strap 222 having at a first end a locking arrangement 224 adapted to receive and engage the opposite end of strap 222 at the serrated inner surface 226 of strap 222 for self-locking adjustable tightening. The locking arrangement 224 includes a release tab 228 and corresponding serrated surface 330. As may be appreciated, the strap 222 may be controllably tightened about a patient's arm in one-handed fashion. The band 210 further includes a slidably mounted pad 220. The pad 220 corresponds in its skin contacting surface contour to the pad 20 of the earlier described embodiment. The pad 220 is, however, not fixedly attached to along the length of strap 22. More particularly, the pad 220 includes slots 220a which slidably receive the strap 22 in the vicinity of locking arrangement 224. FIGS. 11 and 12 further illustrate the pad 220 separately as including the slots 220a and the skin contacting surface contour as previously described. Laterally extending from the strap 222 are nubs 221 for restricting movement of the slidably mounted pad 220 therebetween. In particular, a first pair of nubs 221 are near the locking arrangement 224 and a second pair of nubs 221 are spaced along a length portion of strap 222 and permit movement of the pad 220 only along that portion of strap 222.

Figure 13:
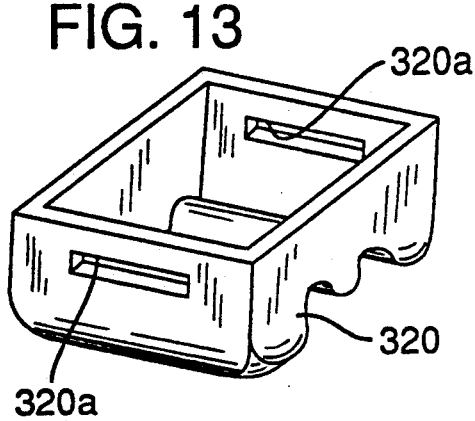
FIGS. 13 and 14 show a second alternative embodiment of the present invention also allowing slidable mounting of the hemostasis pad upon a band.
Figure 14:
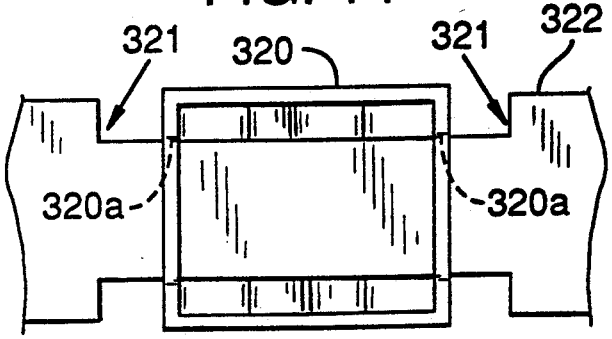

FIGS. 13 and 14 illustrate a third embodiment of the present invention also providing a range of movement of a pad 320 upon a strap 322. In FIGS. 13 and 14, the pad 320 is similar to the pad 220 of FIG. 10 in that it includes slots 320a. The strap 322 includes a length portion 321 of reduced width which corresponds to the width of slots 320a of pad 320. In this manner, the pad 320 is slidably movable along the length portion 321.

The slidable mounting of the pads 220 and 320 of the embodiment of FIG. 10 and FIG. 13, respectively, allow more versatile placement of the bands upon the patient's arm. As may be appreciated, the plastic material used to construct the band 10 may be pliable enough to allow dismounting of the pads 220 and 320. Such dismounting allows the reversal of the pad to orient the notch 44 either up or down the patient's arm. In this manner, the band may be adapted to accommodate either the up or down orientation of the needle in the arm or the righthanded/lefthanded nature of the medical attendant. In any event, the orientation of the notch 44 in all of the illustrated embodiments could be varied and a user could select an appropriate notch 44 orientation from an inventory of bands 10.

The bands as illustrated herein may be formed of substantially transparent material. Transparency aids in the desired relative alignment of the pressure pad and the needle site.

Cheeks 40 provide a depth control function of the pad 20. In particular, by suitably dimensioning the depth of channel 42 relative to vessel 16, the pressure at needle site 18 is taken primarily by the skin surface on each side of vessel 16 and occlusion of the vessel 16 is avoided by its placement within channel 42. In this regard, the ridge 52 should be either flush with or below the cheeks 40. In the illustrated embodiment of FIG. 3, the height of ridge 52 is ⅔ that of the cheeks 40, i.e., the ridge 52 occupies ⅔ of the height of channel 42. The size of channel 42 relative to vessel 16 as illustrated in FIG. 2 is typical of the desired depth control function.

A modification which may be employed in the embodiment of FIGS. 1-9 is illustrated in phantom in FIG. 7. In FIG. 7, the interconnection between the strap 22 and the pad 20 and between the pad 20 and locking arrangement 24 may be angled as indicated in phantom to more closely follow the rounded contour of the patient's arm 12. In the embodiments of FIGS. 10 and 13, the continuous curvature of the band through the slots of the movable pads allows the band to more closely follow the rounded contour of the patient's arm in the vicinity of the pad.

Thus a hemostasis pressure pad band has been shown and described in various embodiments. The hemostasis pressure pad band of the present invention is more conveniently mounted upon a patient's arm during needle removal and more efficiently, i.e., more quickly, achieves hemostasis. As a result, the medical attendant may quickly remove a needle from a patient's arm and be confident that the proper pressure is being applied to the needle site to prevent bleeding. In a short time, e.g., on the order of 2 to 3 minutes, hemostasis is achieved and the band may be removed.

It will be appreciated that the present invention is not restricted to the particular embodiments that have been described and illustrated herein, and that variations may be made without departing from the scope of the invention as found in the appended claims and equivalence thereof.

What is claimed is:

1. A hemostasis pressure pad band comprising:
   a strap including a tightening mechanism for adjustably tightening the strap about a patient's arm in the vicinity of a needle site; and
   a pad coupled to said strap including a skin contacting surface carrying a pair of cheeks defining an open ended channel therebetween and including a base therealong coupling said cheeks whereby a vessel of the arm may be positioned along the channel and the strap may be adjustably tightened to bear the pad suitably against the needle site at the time of needle removal.

2. A hemostasis pressure pad band according to claim 1 wherein said pad includes a notch formation adjacent one end of said channel to accommodate an inclined orientation of a needle relative to the arm.

3. A hemostasis pressure pad band according to claim 1 wherein said channel includes a ridge formation along said base thereof.

4. A hemostasis pressure pad band according to claim 1 wherein said pad includes a notch formation adjacent one end of said channel and includes a ridge formation along said base of said channel.

5. A hemostasis pressure pad band according to claim 4 wherein said ridge formation terminates in a semi-conic contour adjacent said notch formation.

6. A hemostasis pressure pad band according to claim 1 wherein said pad is slidably mounted along a length portion of said strap.

7. A hemostasis pressure pad band according to claim 1 wherein said tightening mechanism is a self-locking mechanism.

8. A hemostasis pressure pad band according to claim 1 wherein the dimension of said channel as defined by said cheeks and said base is with reference to the dimension of said vessel whereby said cheeks and said base perform a depth gauge function to limit pressure applied to the vessel.

9. A hemostasis pressure pad band according to claim 1 wherein said open ended channel is a concave-convex formation.

10. A hemostasis pressure pad for application to a vessel access needle site of a patient in aid of hemostasis, the skin contacting portion of the pad comprising:
    a first cheek; and
    a second cheek, the first and second cheeks defining therebetween an open ended channel including a base whereby the vessel may be positioned along the channel with the first and second cheeks and the base bearing against the needle site.

11. A hemostasis pressure pad according to claim 10, further comprising:
    a band carrying said pad whereby said band may encircle an appendage of the patient and bring said pad against said needle site.

12. A hemostasis pad according to claim 11 further comprising a selectively adjustable tightening arrangement for the band whereby selective tightening of the band about the appendage achieves selective magnitude pressure of said pad against said needle site.

13. A hemostasis pad according to claim 12 wherein said tightening arrangement includes a first serrated surface of the band and a locking tab including a second serrated surface bearing against said first serrated surface in self-locking engagement of the band, the band being selectively adjustable by movement of tightening movement of the first serrated surface relative to the second serrated surface and by loosening movement of the first serrated surface following disengagement of the second serrated surface.

14. A hemostasis pad according to claim 10 wherein said pad further includes a ridge formation along the base of said channel and bearing against said needle site in placement of said pad thereagainst.

15. A hemostasis pad according to claim 14 wherein ridge formation terminates in a semi-conic formation at a leading end of said channel and said cheeks further define at the leading edge of said pad a notch for accommodating an inclined orientation of said needle relative to said needle site while placing said pad against said needle site.

16. A hemostasis pressure pad band comprising:
    a hemostasis pressure pad for application to a vessel access needle site of a patient in aid of hemostasis, the skin contacting portion of the pad comprising a first cheek and a second cheek, the first and second cheeks defining therebetween an open ended channel including a base whereby the vessel may be positioned along the channel with the first and second cheeks and the base bearing against the needle site; and
    a band carrying said pad whereby said band may encircle an appendage of the patient and bring said pad against said needle site.

17. A hemostasis pressure pad band according to claim 16 further comprising a selectively adjustable tightening arrangement for the band whereby selective tightening of the band about the appendage achieves selected magnitude pressure of said pad against said needle site.

18. A hemostasis pressure pad band according to claim 17 wherein said tightening arrangement includes a first serrated surface of the band and a locking tab including a second serrated surface bearing against said first serrated surface in self-locking engagement of the band, the band being selectively adjustable by movement of tightening movement of the first serrated surface relative to the second serrated surface and by loosening movement of the first serrated surface following disengagement of the second serrated surface.

19. A hemostasis pressure pad band according to claim 16 wherein said pad further includes a ridge formation along the base of said channel and bearing against said needle site in placement of said pad thereagainst, the ridge formation terminating in a semi-conic formation at a leading end of said channel, said first and second cheeks further defining at the leading edge of said pad a notch for accommodating an inclined orientation of said needle relative to said needle site while placing said pad against said needle site.

20. A hemostasis pressure pad band comprising:
    a strap including a tightening mechanism for adjustably tightening the strap about a patient's arm in the vicinity of a needle site, the tightening mechanism being a self-locking mechanism, said self-locking mechanism including first and second opposing serrated surfaces, the first serrated surface being on a distal length portion of the strap and the second serrated surface being on a locking tab bearing against said first serrated surface when said tightening mechanism engages said strap; and a pad coupled to said strap including a skin contacting surface carrying a pair of cheeks defining an open ended channel therebetween whereby a vessel of the arm may be positioned along the channel and the strap may be adjustably tightened to bear the pad suitably against the needle site at the time of needle removal.

* * * * *